(12) United States Patent
Mujat et al.

(10) Patent No.: US 8,911,144 B2
(45) Date of Patent: Dec. 16, 2014

(54) OPTICAL COHERENCE TOMOGRAPHY (OCT) FREEZE DRYING MICROSCOPY

(75) Inventors: Mircea Mujat, Acton, MA (US); William J. Kessler, Groton, MA (US)

(73) Assignee: Physical Sciences, Inc., Andover, MA (US)

( * ) Notice: Subject to any disclaimer, the term of this patent is extended or adjusted under 35 U.S.C. 154(b) by 170 days.

(21) Appl. No.: 13/454,720

(22) Filed: Apr. 24, 2012

(65) Prior Publication Data

US 2012/0294328 A1 Nov. 22, 2012

Related U.S. Application Data

(60) Provisional application No. 61/487,168, filed on May 17, 2011.

(51) Int. Cl.
| | |
|---|---|
| *G01N 25/02* | (2006.01) |
| *G01J 5/00* | (2006.01) |
| *G01K 7/00* | (2006.01) |
| *G01K 13/00* | (2006.01) |
| *G01N 21/47* | (2006.01) |

(52) U.S. Cl.
CPC ................................ *G01N 21/4795* (2013.01)
USPC ............. 374/16; 374/141; 374/121; 374/124; 374/179; 374/183

(58) Field of Classification Search
USPC ......... 374/141, 120, 121, 208, 179, 183, 185, 374/16, 17, 19, 119, 124, 130, 137, 374/601–613, 625–640
See application file for complete search history.

(56) References Cited

U.S. PATENT DOCUMENTS

| | | | | |
|---|---|---|---|---|
| 5,655,839 | A * | 8/1997 | Schmidt et al. | 374/132 |
| 7,520,667 | B2 * | 4/2009 | Pahlsson et al. | 374/45 |
| 2003/0011779 | A1 | 1/2003 | Swanson | |
| 2005/0002435 | A1 * | 1/2005 | Hashimoto et al. | 374/43 |
| 2006/0053652 | A1 | 3/2006 | Gyory et al. | |
| 2006/0256343 | A1 | 11/2006 | Choma et al. | |

OTHER PUBLICATIONS

Huang, et al., "Optical Coherence Tomography," Science, v. 254, Issue 5035, pp. 1178-1181, 1991.
Tchessalov, et al., "Development of Freeze Dried Biosynthetic Factor VIII: I. A Case Study in the Optimization of Formulation," Pharmaceutical Development and Technology, v. 14, issue 6, pp. 687-697, 2009.
Pikal, "Lyophilization," Encyclopedia of Pharmaceutical Technology, v. 6, pp. 1299-326, 2002.
Pikal, et al., "The Collapse Temperature in Freeze Drying: Dependence on Measurement Methodology and Rate of Water Removal From the Glassy Phase," International Journal of Pharmaceutics, v. 62, pp. 165-186, 1990.
Pikal, et al., "The Effects of Formulation Variables on the Stability of Freeze-Dried Human Growth-Hormone," Pharmaceutical Research, v. 8, Issue 4, pp. 427-436, 1991.
Podoleanu et al., "Three Dimensional OCT Images from Retina and Skin," Optics Express, v. 7, Issue 9, pp. 292-298, 2000.
The International Search Report for PCT Application No. PCT/US2012/034918, mailed on Aug. 16, 2012 (5 pgs).

* cited by examiner

*Primary Examiner* — Mirellys Jagan
(74) *Attorney, Agent, or Firm* — Proskauer Rose LLP

(57) ABSTRACT

A product critical temperature during freeze drying is determined. The product is imaged using optical coherence tomography ("OCT"). The product is freeze dried while the temperature of the product is measured. The product critical temperature is the temperature at which a product structure event occurs during freeze drying.

11 Claims, 3 Drawing Sheets

OPTICAL COHERENCE TOMOGRAPHY (OCT) FREEZE DRYING MICROSCOPY

CROSS-REFERENCE TO RELATED APPLICATIONS

This application claims the benefit of and priority to U.S. provisional patent application No. 61/487,168, filed May 17, 2011, the entire contents of which are incorporated by reference herein.

FIELD OF THE INVENTION

This invention relates generally to microscopy, and more particularly, to freeze drying microscopy using optical coherence tomography to provide three-dimensional images of a chemical as it is being freeze dried.

BACKGROUND

Biopharmaceuticals are generally administered through venous, intramuscular or subcutaneous injections (e.g., parenteral drug delivery). Oral delivery is not typically used because often proteins are adversely affected by or poorly absorbed (due to their large size and instability) through the gastrointestinal tract. Thus, many new biotechnology drugs, including those used for the treatment of cancer, are formulated and produced using the freeze-drying process. Freeze drying (e.g., lyophilization) produces stable drug products that can be stored and reconstituted for patient use. Although drying stabilizes the active pharmaceutical ingredient for long term storage, freeze-drying exposes proteins to numerous in-process degradation processes that can have adverse effects on the drug efficacy. To prevent these degradation processes, pharmaceutical companies produce drug specific formulations and use freeze-drying processes that ensure that the final product has a high level of purity and has a targeted two-year shelf life.

The development of biological drugs often requires product formulations that must be lyophilized to produce stable products, which can be stored in vials and reconstituted for patient use. Lyophilization is the process of drying (e.g., removing water from) a pharmaceutical compound by freezing it first and then sublimating the ice. An important process design parameter is the product temperature during primary drying which is typically set at or below the temperature at which the product undergoes structural collapse during primary drying (e.g., the collapse temperature ("$T_c$")). $T_c$ is the temperature at which the amorphous pharmaceutical formulation being dried undergoes viscous flow resulting in structural collapse. When the product formulation is frozen during the freeze drying process, pores form, which cause the ice formation to appear to have a sponge or cake-like structure. During the primary drying phase of the freeze drying process, as the product temperature approaches $T_c$, viscous flow within the product structure can occur with the pores getting larger. There are different levels of structural change, which include micro-collapse (which can be tolerated) and complete collapse. During the lyophilization of pharmaceutical products manufacturers seek to avoid collapse to ensure elegant appearance of the freeze dried cake, low residual water content, storage stability and positive reconstitution characteristics.

Current light transmission based freeze drying microscopy ("LT-FDM") systems are limited to estimating $T_c$ using 1-2 μL, liquid product samples frozen between microscope slides, resulting in a frozen product thickness of 50-100 μm. These samples do not always provide accurate collapse temperature determinations due to differences in ice nucleation rates, crystallization tendencies for solutes, frozen product structures and drying rates as compared to samples prepared and freeze dried in vials. Furthermore, LT-FDM samples are not representative of samples dried in vials, which can have thicknesses of 5-50 mm.

Thus, current LT-FDM techniques do not accurately estimate $T_c$ for freeze drying in a container of practical significance. Literature studies suggest that the differences in $T_c$ between current FDM and vial drying are typically several degrees, which results in a 25% increase in primary drying time for every 2° C. decrease in product processing temperature. A 25% increase in time can significantly impact the economic viability of a process that can require 1-4 days under ideal processing conditions, without the increase in time due to overly conservative process conditions used due to a lack of knowledge of the product formulation collapse temperature.

SUMMARY OF THE INVENTION

The invention features a method and device that can provide three-dimensional ("3D") product structural information during freeze drying. An advanced Optical Coherence Tomography based Freeze Drying Microscopy system ("OCT-FDM") can measure the 3D product structure for product formulations frozen in standard product vials. OCT-FDM can be used to determine collapse temperature, eutectic temperature, skin formation, annealing effects and drying rates. Typical product samples can include drug products, such as vaccines, anti-cancer therapies, etc. Drug production costs can be reduced through the development of more efficient lyophilization processes, potentially providing new biotech therapies to a wider patient population.

In one aspect, there is a method of determining a product critical temperature during freeze drying. The method includes imaging a product using OCT while freeze drying the product. The method also includes measuring temperature of the product during freeze drying. The product critical temperature is determined by determining the temperature at which a product structure event occurs during freeze drying.

In another aspect, there is a method of providing three-dimensional structural information about a sample during freeze drying. The method includes freeze drying the sample. A three-dimensional image of the sample is acquired. The three-dimensional structural information about the sample is determined from the three-dimensional image.

In yet another aspect, there is a system for determining a product critical temperature during freeze drying. The system includes a freeze dryer including a holder for a product. The system also includes a temperature sensor coupled to the product. A three-dimensional imager includes a source of radiation, and a detector that are positioned proximate to the holder. A processor is coupled to the detector of the three-dimensional imager and is configured to receive images from the three dimensional imager, receive information about product temperature from the temperature sensor during freeze drying, and determine the product critical temperature by determining a temperature at which a product structure event occurs during freeze drying.

In another aspect, there is a system for measuring three-dimensional structural information of a sample during freeze drying. The system includes a freeze dryer including a holder for the product. A three-dimensional imager including a source of radiation and a detector is positioned proximate to the holder. The system also includes a processor coupled to the detector of the three-dimensional imager. The processor is configured to receive images from the three dimensional imager. A determination is made by the processor regarding the three-dimensional structural information about the sample from the images.

Each aspect described above can include one or more of the following features. In some embodiments, the product structure event is a loss of product structure formed during freezing and the product critical temperature is a product collapse temperature. In various embodiments, the product structure event is one or more elements forming the product solidifying and forming the product structure, while at least one of more elements forming the product remains liquid and the product critical temperature is a product eutectic temperature. The product critical temperature can be either a product collapse temperature or a product eutectic temperature.

In various embodiments, the product can be freeze dried in a standard product vial. A vial (e.g., the standard product vial) can have a diameter of about 5 mm to about 50 mm. The holder can be configured to hold one or more vials capable of containing the product. The holder can also be configured to hold a standard product vial. In other embodiments, the product can be freeze dried in a thin film within a vial or between glass or plastic slides.

A thermocouple, resistance temperature detector ("RTD") or an infrared thermometer can be used to measure the product temperature or monitor product temperature. The thermocouple can be configured to contact the product.

In some embodiments, the three-dimensional image of the sample can be acquired using OCT. The three-dimensional imager (e.g., an OCT system) can be configured to image the product contained in a standard product vial. The three-dimensional structural information can include information about ice nucleation during freeze drying. The three-dimensional structural information can also include information about sublimation of solvents from the sample during freeze drying. In addition, the three-dimensional structural information can include information about the sample structure formed during a freezing phase and lost due to micro-collapse or collapse during the primary drying phase of the freeze drying process. Images of the sample can be acquired at multiple depths.

Other aspects and advantages of the invention will become apparent from the following detailed description, taken in conjunction with the accompanying drawings, illustrating the principles of the invention by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

DETAILED DESCRIPTION OF THE INVENTION

Figures 1A, 1B, 1C:
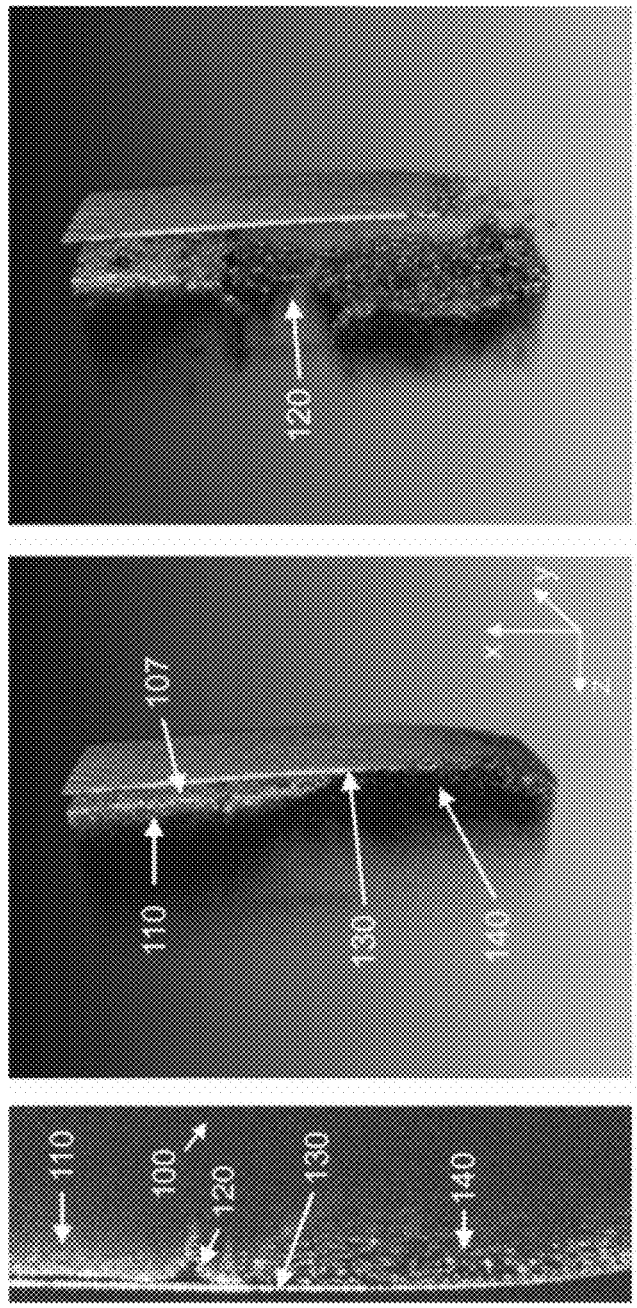
FIG. 1A is a two-dimensional image of a freeze dried product structure.
FIG. 1B is a three-dimensional image of a freeze dried product structure near the surface of the vial.
FIG. 1C is a three-dimensional image of a freeze dried product structure away from the surface of the vial following viscous flow and structural collapse.

A freeze dryer and an OCT system can be combined to form a microscopy system for taking both two-dimensional and three-dimensional images of samples. The system provides real time, non-intrusive determination of pharmaceutical product structure and combined with product temperature measurements, a determination of the critical product temperature (e.g., the collapse temperature) during freeze drying in a relevant product container. The system can also provide visualization and monitoring of the ice crystal formation during the freezing phase, which influences the product drying efficiency. This temperature determination can be used to improve processing efficiency and significantly shorten the processing time.

The first step in a freeze drying cycle is the freezing process, which is typically accomplished by lowering the freeze dryer shelf temperature and thus the vial (and product) temperature from room temperature to approximately $-40°$ C. Depending on the formulation, the rate of the temperature change can significantly influence the formation and size of the ice crystals, which can influence the product drying rate and the dry product pore structure during the drying process. Larger pores allow water vapor to escape easier than smaller pores, allowing for a more efficient and faster drying process.

Once the product reaches the desired freezing temperature, the ice sublimation process is initiated by lowering the pressure in the product chamber using a cryogenic condenser (typically $-70°$ C.) and vacuum pumping system. Heat is then applied to the shelf or shelves that hold the product vial(s) to sublime the product ice. If the product ice sublimation interface temperature at which the sublimation process is performed is below the collapse temperature, the final product maintains the pore structure established during the freezing phase. If the product ice sublimation interface temperature of the product is at or above the collapse temperature, the product can undergo viscous flow and the structure established during freezing collapses. Product collapse can lead to non-elegant final product, increased product residual moisture content, reduced stability and increased reconstitution time. Process product temperatures slightly below the collapse temperature are desired for efficient processes that produce pharmaceutically elegant products with low residual moisture and good product storage stability and reconstitution times; therefore, the collapse temperature needs to be precisely known.

OCT is the optical analog of ultrasound and is an advanced cross-sectional imaging technique. Cross-sectional imaging is done by the measurement of the magnitude and echo time delay of backscattered light. Image resolutions of ~1 to ~15 µm can be achieved, and imaging can be performed in situ and in real time. The incident light beam is directed at the object to be imaged, and the time delay and magnitude of backscattered or back reflected light is measured. The beam is scanned axially and in the transverse direction, and rapid successive axial measurements are performed. The result is a 3D data set, which represents the optical reflection or backscattering of the material or tissue. The 3D structure of the sample can be constructed from the measured dataset.

A typical fiber optic version of an OCT system can, for example, include a Michelson interferometer formed with the 2×2 fiber coupler that has a mirror in the reference arm and a focusing lens in the sample arm. A short temporal coherence length super luminescent diode ("SLD") can be used as a light source. Interference fringes are obtained as the light from the reference arm interferes with light backscattered from the sample. Only the light backscattered from a depth of the sample that corresponds to the reference arm and the sample arm being equal to within the coherence length of the light source (~3-15 µm) contributes to the interference fringes while the rest of the detected light generates a DC background. The magnitude of the fringe envelope gives the sample reflectivity at that specific depth.

In FIG. 1A, a two-dimensional image of a freeze dried product structure 100 is shown. The freeze dried product structure 100 includes a dry portion 110 and a frozen portion 140 can comprise. Using OCT, an image of the freeze dried product structure 100 can be taken through a surface 130 of a container.

FIG. 1A shows a collapse event of the freeze dried product structure 100. A collapse 120 is evidenced by loss of product structure or by the formation of cracks while the product is freeze dried. A collapse can occur during the drying process and is typically located adjacent to the sublimation front just below collapse 120.

FIGS. 1B and 1C show a three-dimensional view of the collapse event. FIG. 1B shows not only the surface 130 of the container, the dry portion 110, the frozen portion 140, but also a detachment portion 107 typically referred to as product shrinkage. The detachment portion 107 is a part of the product that has broken apart from the rest of the surface 130. FIG. 1C shows the collapse 120, which for this product formulation occurred behind the detachment portion 107. A collapse temperature is the temperature at which the collapse 120 first occurs.

In addition to a collapse temperature, a eutectic temperature can be determined. The eutectic temperature is the temperature at which a crystalline product undergoes melting and loss of structure. In contrast to the collapse of an amorphous product which occurs adjacent to the sublimation front as it proceeds through the sample, a eutectic melt occurs throughout the frozen (non-dried) portion of the product sample. Using the OCT microscopy system, the eutectic temperature of a sample can be determined. Using similar techniques, the OCT microscopy system can also be used to determine a product skin formation.

The system can also perform imaging of the product for visualization and monitoring of ice crystal formation during the freezing process and for visualization and monitoring of the product structure during primary and secondary drying. The structure of the ice crystals determines the pore structure characteristics during the drying process and is of significant interest because the structure directly influences the product resistance to drying and the process efficiency. During primary drying, the collapse temperature of amorphous products is defined as the temperature at which viscous flow in the product structure occurs resulting in cracks and large pores or holes showing up in the product representing structural collapse.

Annealing effects on ice structures, solute crystallization indicating phase transitions and other critical temperatures can also be observed using the system. Relative rates of drying for different formulations or at different temperatures can also be used to be determined using the system.

Figure 2:
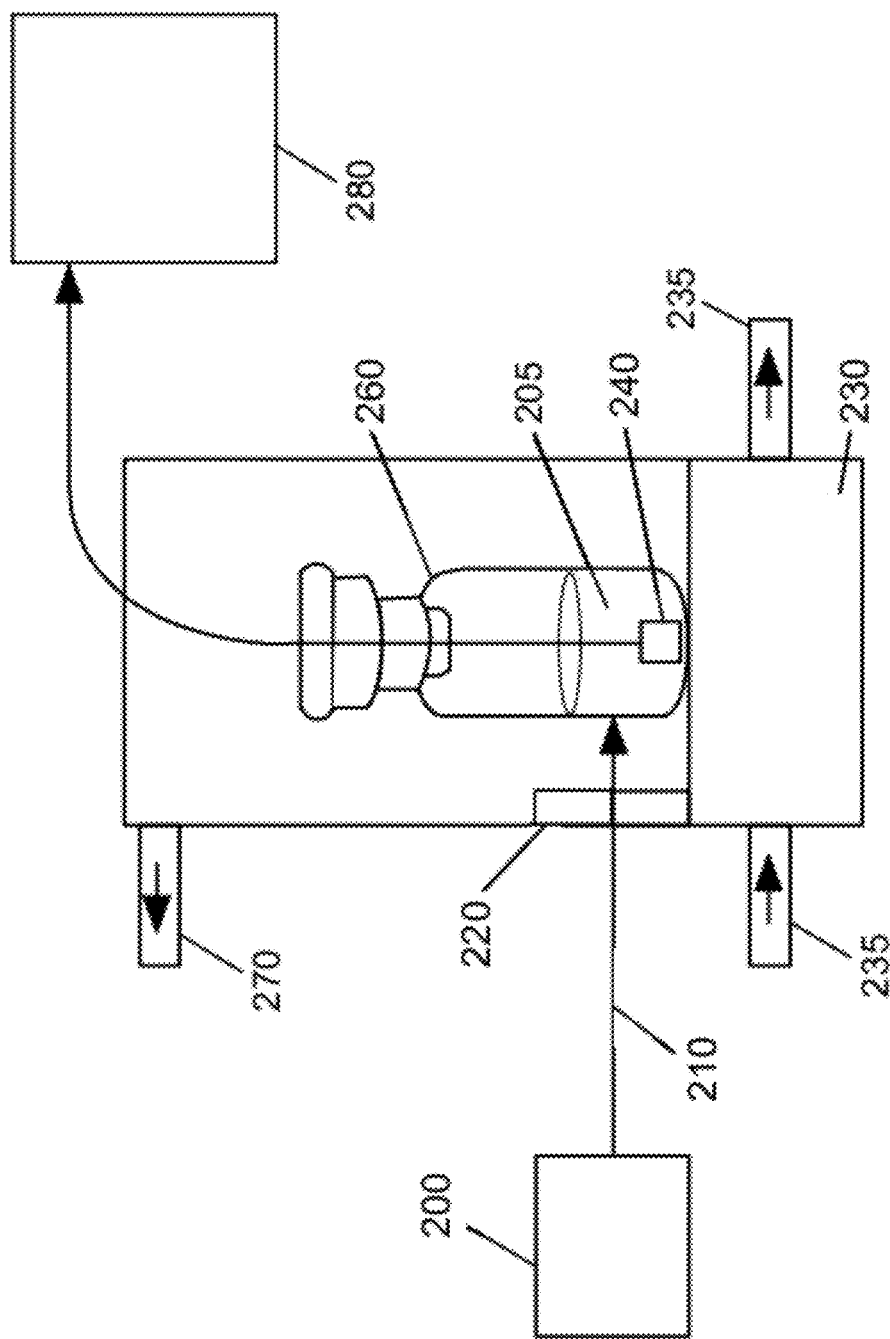
FIG. 2 is a diagram of a freeze drying microscopy system using OCT for the measurement of the 3D product structure for product formulations frozen in standard product vials.

In FIG. 2, a freeze drying microscopy system using OCT for the measurement of the 3D product structure for product formulations frozen in standard product vials is shown. Scanning optics 200 are used to view and image a product 205. The scanning optics 200 can include an OCT system that directs an OCT beam 210 towards a window 220. The OCT beam 210 can then be scanned so that the OCT beam can view different parts of the product 205. In this example, the product 205 is contained in a vial 260. A temperature sensor 240 is used to monitor the product 205 temperature near the bottom of the vial 260. A temperature control block 230 freeze dries the product 205 while it is contained in the vial 260. The temperature control block can control the amount of cooling agent 235 that flows through to ensure that the product 205 freezes. Examples of cooling agent 235 are gas vapor from dry ice or liquid nitrogen or liquid cryogens such as ethanol. Alternatively the temperature control block can be cooled and warmed using thermoelectric coolers ("TEC"). The vial 260 can be a vial of any size. In some examples, the vial can have a diameter of ~5 mm to ~50 mm. For example, the vial can be a standard product vial. The solvent can be water or an organic solvent, such as methanol, ethanol, tertiary butyl alcohol, acentonitrile, or other solvents commonly used in a manufacturing process.

Freeze dryer system components can include the freeze dryer: drying chamber, product shelf (shelves of multi-vial dryers), heat transfer system, cooling system, condenser, vacuum pumping system, and process control instrumentation. One side of the freeze dryer can include an anti-reflective coating glass window for OCT measurements.

The drying chamber can include a miniature, stainless steel, quick-flange six-way asymmetric or symmetric cross that can house a single dryer shelf made of a thermally controlled aluminum block. The block temperature can be controlled by a TEC (e.g., the temperature control block 230 of FIG. 2) backed by a plate that can be cooled using a cryostate circulating coolant liquid at ~−8° C. This assembly can achieve thermal block temperature adjustment from <−40° C. to >20° C. by controlling the TEC cooler using a computer. A vacuum pump 270 can be used to control the pressure within the freeze drying microscopy system.

The temperature sensor 240 can be a thermocouple placed within the product at the bottom center location for the determination of the product temperature. In addition, one or more thermocouples can be placed on the shelf (block) surface to provide temperature measurements for real-time thermal control. The product vial can be placed on top of the block to mimic the architecture typically used within the pharmaceutical industry. The six-way cross vacuum chamber can be outfitted with pressure monitoring instruments (e.g., Pirani gauge and/or capacitance manometer), a vacuum pumping port, and a condenser unit (e.g., liquid nitrogen dewar) for pressure control. The temperature sensor 240 can be connected to a temperature monitor 280 to check or record the temperature of the product 205 at any given time.

In some embodiments, the temperature sensor 240 is an infrared thermometer, a RTD, a wireless RTD or a thermocouple. Multiple temperature sensors can be used to monitor temperature at various positions within the vial 260. The various positions can include near the top of the product 240, in the middle of the product 240, or at the bottom of the product 240. Drying of products occurs from the top to the bottom, and product temperature varies at different heights. The temperature difference between the top and bottom of the product can be typically ~1° C. Measuring at different positions near the sublimation front can more accurately determine $T_c$. Measuring with multiple temperature sensors is not limited to measuring at different heights and can include measuring at random points within the product 240. The multiple temperature sensors can also include one or more types of temperature sensors.

The single vial freeze dryer, or a freeze dryer that can house standard pharmaceutical vials, allows controlled product freezing and water sublimation through temperature ramping. Although a single vial freeze dryer is described above, the system is not limited to just imaging samples in a single vial. The system can be used to image samples created as thin films within a vial or between glass or plastic slides without any sort of container. The system can also utilize any sort of holding mechanism.

The OCT system, which can be included in the scanning optics 200, can be configured to include several scan modes: 1) a single frame x-z scan mode can be used for sample alignment after a vial is introduced in the freeze-dryer chamber to bring the vial-product interface (e.g., the inner vial surface) close to the side of the imaging window. This scan mode allows for the determination of the optimum axial (z) limits of the 3D scan volume. 2) A second scan mode allows for a single 3D scan volume in en-face mode (x-y first and then step axially). 3) The standard measurement scan mode allows for scanning 3D volumes synchronized with the freeze-drying temperature control. The number of temperature steps (and therefore of the 3D volumes to be acquired) can be set first, and then after each OCT volume scan can a digital signal be sent to the freeze-dryer hardware control to step and hold the dryer shelf temperature at the next value. OCT software can wait until the freeze-dryer hardware control returns a signal indicating that the required temperature had been reached. Afterwards, the OCT system can continue with the next volume scan. In some embodiments, the scan mode can be done using any type of spectral scan where imaging is done in a two-axis plane (e.g., x-y, y-z, or x-z planes) and stepped in the third axis (e.g., z, x, or y, respectively). These spectral scans can be compiled to produce 3D images. An example of the x-y-z coordinate system can be found in FIG. 1B.

Figure 3:
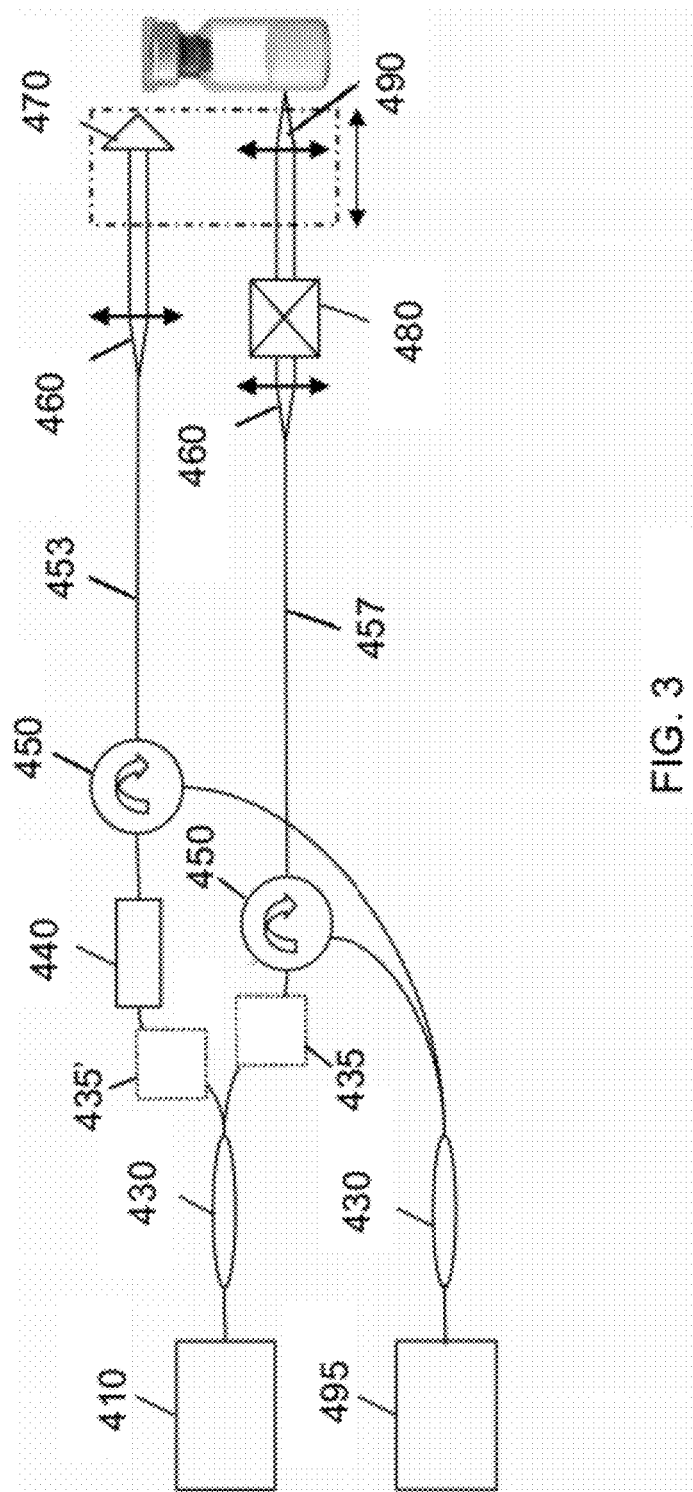
FIG. 3 is a diagram of a time domain OCT setup.

In FIG. 3, a time domain OCT setup is shown. In the time domain implementation of OCT ("TDOCT"), a scanning mechanism is used in a reference arm 453 of the interferometer to build up the depth reflectivity profile, and a scanning mechanism in a sample arm 457 provides lateral scan. TDOCT is the OCT technique in which one voxel, or volumetric pixel, is measured at a time and multiple voxels are measured sequentially covering a scan volume. The final result is a 3D volume scan.

A superluminescent diode 410 is used to provide fiber coupled light to a fiber splitter 430. The fiber splitter 430 passes the fiber coupled light through one or more fiber circulators 450. The light output from the fibers along reference arm 453 and sample arm 457 is collimated using fiber collimators 460. At least one beam then passes through a retroreflector 470. At least one beam passes through lateral scanning optics 480 and a microscope objective 490.

Once the beams reach the product, light is reflected back to the fiber collimator, and back through the one or more fiber circulators 450, through alternate beam paths to a different fiber splitter/combiner 430. The beams are coupled and sent to a detector 495, which detects the signal intensity and is used to create an image of the product. In TDOCT, the detector 495 could be a balance detector and both outputs of the fiber splitter/combiner 430 are used as inputs into the detector 495.

The pores in a freeze dried pharmaceutical product can range from several microns to tens of microns. The OCT instrument can provide 2-5 µm lateral resolution and 7-10 µm axial imaging resolution when imaging the pore structure (assuming a sample average refractive index of 1.38 and a scanning area of ~4 mm×~0.75 mm lateral (en-face)). In addition, since the freeze drying process can result in product structures that can be different at the vial/product interface as compared to inside the bulk product, the imaging depth is ~1.5 mm (800×150×200 pixels). This can result in the capture of structural information beyond the vial wall interface, eliminating uncertainty regarding the value of the information and how it pertains to the bulk drying characteristics of the pharmaceutical product formulation. A TDOCT instrument can have dynamic focusing at 1.3 µm, which can ensure deep penetration and proper focus across the imaging window into the sample. However, the TDOCT instrument is not limited to viewing at 1.3 µm and can have dynamic focusing alignment at any wavelength.

The system can achieve 3D scanning using two galvanometers and a translation stage. A coordinate system defines an x-axis and a y-axis in a plane perpendicular to the incident laser beam (en-face image) and a z-axis along the incident beam. A scanning protocol can be used to define an x-axis for fast scanning, a y-axis for slower scanning, and a z-axis for the slowest scanning. This approach relaxes the requirements on the speed of the dynamic focusing. This way, the depth scanning can be made simply using a motorized translation stage. However, since there is no option for a fast z scanning, an alternative method is needed to create a carrier for the interference fringes. An acousto-optic phase modulator ("AOM") 440 in the reference arm 453 can be used to provide this capability. In some embodiments, there can be two AOMs 440. One AOM 440 can be located in the reference arm and the other AOM 440 can be located in the sample arm.

If there is a dispersion mismatch between the reference arm 453 and the sample arm 457, a crystal or amorphous material transmitting infrared radiation ("AMTIR") window can be inserted in either cell 435' of the reference arm 453 or cell 435 of the sample arm 457 so that the dispersion is matched. In some embodiments, if a second AOM is used (e.g., in cell 435), there is no need for an AMTIR window.

As shown in FIG. 3, for dynamic focusing, the retroreflector 470 and microscope objective 490 are placed on the same motorized translation stage. Moving the retroreflector in the reference arm 453 simultaneously with the microscope objective relative to the sample, ensures that the focus and the coherence gate are maintained overlapped.

The system can measure 3D product structures with a resolution of ~5-10 µm and a measurement depth of ~2 mm in ~5-50 mm thick frozen product samples. Optical imaging measurements can be made through the side of the vial allowing tracking of the continuously moving dry interface zone that is of critical importance when determining collapse temperature.

To provide three-dimensional structural information about a sample during freeze drying, a three-dimensional image of the sample can be acquired (e.g., using OCT) while the sample is being freeze dried. The three-dimensional structural information can be determined from the three-dimensional image. The product critical temperature can be the temperature at which a product structure event occurs during freeze drying.

For a system to determine a product critical temperature during freeze drying, the system can include a freeze dryer including a holder for a product, a temperature sensor coupled to the product, a three-dimensional imager including a source of radiation and a detector is positioned proximate to the holder, and a processor coupled to the detector of the three-dimensional imager. The processor can be configured to receive images from the three dimensional imager, receive information about product temperature from the temperature sensor during freeze drying, and determine the product critical temperature by determining a temperature at which a product structure event occurs during freeze drying. The three dimensional imager can take both two-dimensional and three-dimensional images.

For a system to measure three-dimensional structural information of a sample during freeze drying, the system can include a freeze dryer including a holder for the product, a three-dimensional imager including a source of radiation and a detector positioned proximate to the holder, and a processor coupled to the detector of the three-dimensional imager. The processor can be configured to receive images from the three dimensional imager. A determination is made by the processor regarding the three-dimensional structural information about the sample from the images.

The product structure event can be a number of events. The product structure event can be a loss of product (or cake) structure and the product critical temperature is a product collapse temperature if the product is amorphous and the product critical temperature is a product eutectic temperature if the product is crystalline. The three-dimensional structural information can include information about ice nucleation during freezing, a phase transition event, sublimation of the sample during drying, and/or a change of sample structure formed during a freezing phase and lost during the drying phase freeze drying. Images of the sample can be acquired at multiple depths.

In some examples, the imaging system can use other types of OCT. These types can include spectral-domain OCT ("SDOCT"), Fourier domain OCT ("FDOCT"), and full-field OCT ("FFOCT"). Using SDOCT (or FDOCT), individual spectral components of light are detected simultaneously by use of a spectrometer and a charge-coupled device ("CCD") array. SDOCT/FDOCT is an OCT technique in which a whole depth profile (e.g. a large number of voxels) is measured simultaneously. Fourier transforming the detected spectral interference directly provides the reflectivity depth profile without the need of depth scanning or frequency modulation as in the TDOCT. Another variation of FDOCT, called swept source OCT, uses a single point detector and a wavelength sweeping source to achieve the same result (i.e. recording of the spectrally resolved interference signal). Because the depth profile is acquired during the integration time of the linear detector (or during a complete sweep of the wavelength), line rates of tens or hundreds of kHz, corresponding to video frame rates (30+ fps), are possible. This method achieves at least an order of magnitude increase in imaging speed and sensitivity, as compared to standard time domain detection technology. Spectral domain methods also provide direct access to the spectrum of the optical signal. FFOCT, yet another version of OCT, uses a two-dimensional ("2D") CCD camera to image a transversal slice through the sample with ultra-high resolution (~1-2 µm). Depth scanning is required to image a 3D volume.

Proper focus over a large imaging depth and good lateral resolution are challenging to obtain using a FDOCT system. In addition, the freeze drying process can take hours and even days, and there is no need for ultra-fast measurement speed. Therefore, given the ability of a TDOCT system to accommodate dynamic focusing and the other advantages including improved intensity roll-off and elimination of the complex conjugate image, a TDOCT system can be used, for imaging of the 3D pore structure of the product formulation during a freeze drying process. Dynamic focusing is obtained by moving the microscope objective simultaneously with the reference arm for depth scanning, such that the focal plane of the objective overlaps always with the coherence gate that produces the OCT image. Additional blurring due to multiple light scattering when imaging deep into a turbid medium cannot be avoided even by using dynamic focusing. Lateral resolution degrades with depth.

For Gaussian beams, the depth of focus and the beam waist (lateral resolution) are inversely proportional. To achieve high lateral resolution one has to sacrifice depth of focus. As the entire depth reflectivity profile is acquired simultaneously in FDOCT, only a relatively poor lateral resolution (~10-20 µm) is possible if a large depth of focus (~2-3 mm) is required.

Outside the depth of focus the quality of the OCT is degraded by lateral defocusing. This problem is solved in TDOCT by using dynamic focusing. The in-focus region of the imaging beam is scanned in depth simultaneously with the coherence gate maintaining the proper focus along the whole depth of the scan.

The reflectivity profile exhibits an inherent roll-off with depth in FDOCT due to the finite size of the pixel (~10-15 µm) in the spectrometer. Fourier transforming the rectangular function specific to the CCD pixel generates a sin c function in the spatial (depth) domain that decreases with depth. The result is an inherent reduction of the detected signal with depth of the order of 10-30 dB over 2 mm of imaging depth. The intensity roll-off is significantly reduced in TDOCT.

Fourier components outside the imaging window fold back into the imaging window in FDOCT. Sometimes their magnitude is small enough to not exceed the noise level, but in many cases, spurious reflections in the imaging system can bring significant unwanted Fourier components into the imaging window making it difficult to distinguish between the real image and the complex conjugate image. These effects are not existent in TDOCT allowing for a "cleaner" image.

In addition to the intensity roll-off, the scattering properties of the sample also reduce the detected signal with depth. For highly scattering samples, as is the general case in material science and biomedical applications, this is the limiting factor to the effective imaging depth. In addition to scattering, absorption also limits the effective imaging depth. Scattering decreases as the wavelength increases in the near infrared ("NIR") but water absorption increases. There are several low absorption windows at ~800-900 nm and ~1 µm and these spectral regions are preferred for applications where the sample has significant water content.

Local heating from the OCT setup can be compensated for to ensure that source intensity of equipment does not adversely affect the determination of the $T_c$. This can include compensating for any heat derived from the lasers that are used for scanning a 3D image.

The above-described techniques can be implemented in digital and/or analog electronic circuitry, or in computer hardware, firmware, software, or in combinations of them. The implementation can be as a computer program product, i.e., a computer program tangibly embodied in a machine-readable storage device, for execution by, or to control the operation of, a data processing apparatus, e.g., a programmable processor, a computer, and/or multiple computers. A computer program can be written in any form of computer or programming language, including source code, compiled code, interpreted code and/or machine code, and the computer program can be deployed in any form, including as a stand-alone program or as a subroutine, element, or other unit suitable for use in a computing environment. A computer program can be deployed to be executed on one computer or on multiple computers at one or more sites. The computer program for data and image processing can be implemented in the computer central processing unit ("CPU") or in a graphical processing unit ("GPU") for faster processing. GPU processing could significantly increase the data processing speed which is important for monitoring ice nucleation processes during freezing.

Method steps can be performed by one or more processors executing a computer program to perform functions of the invention by operating on input data and/or generating output data. Method steps can also be performed by, and an apparatus can be implemented as, special purpose logic circuitry, e.g., a FPGA (field programmable gate array), a FPAA (field-programmable analog array), a CPLD (complex programmable logic device), a PSoC (Programmable System-on-Chip), ASIP (application-specific instruction-set processor), or an ASIC (application-specific integrated circuit), or the like. Subroutines can refer to portions of the stored computer program and/or the processor, and/or the special circuitry that implement one or more functions.

Processors suitable for the execution of a computer program include, by way of example, both general and special purpose microprocessors, and any one or more processors of any kind of digital or analog computer. Generally, a processor receives instructions and data from a read-only memory or a random access memory or both. The essential elements of a computer are a processor for executing instructions and one or more memory devices for storing instructions and/or data. Memory devices, such as a cache, can be used to temporarily store data. Memory devices can also be used for long-term data storage. Generally, a computer also includes, or is operatively coupled to receive data from or transfer data to, or both, one or more mass storage devices for storing data, e.g., magnetic, magneto-optical disks, or optical disks. A computer can also be operatively coupled to a communications network in order to receive instructions and/or data from the network and/or to transfer instructions and/or data to the network. Computer-readable storage mediums suitable for embodying computer program instructions and data include all forms of volatile and non-volatile memory, including by way of example semiconductor memory devices, e.g., DRAM, SRAM, EPROM, EEPROM, and flash memory devices; magnetic disks, e.g., internal hard disks or removable disks; magneto-optical disks; and optical disks, e.g., CD, DVD, HD-DVD, and Blu-ray disks. The processor and the memory can be supplemented by and/or incorporated in special purpose logic circuitry.

To provide for interaction with a user, the above described techniques can be implemented on a computer in communication with a display device, e.g., a CRT (cathode ray tube), plasma, or LCD (liquid crystal display) monitor, for displaying information to the user and a keyboard and a pointing device, e.g., a mouse, a trackball, a touchpad, or a motion sensor, by which the user can provide input to the computer (e.g., interact with a user interface element). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributed computing system that includes a front-end component. The front-end component can, for example, be a client computer having a graphical user interface, a Web browser through which a user can interact with an example implementation, and/or other graphical user interfaces for a transmitting device. The above described techniques can be implemented in a distributed computing system that includes any combination of such back-end, middleware, or front-end components.

The components of the computing system can be interconnected by transmission medium, which can include any form or medium of digital or analog data communication (e.g., a communication network). Transmission medium can include one or more packet-based networks and/or one or more circuit-based networks in any configuration. Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), Bluetooth, Wi-Fi, WiMAX, general packet radio service (GPRS) network, HiperLAN), and/or other packet-based networks. Circuit-based networks can include, for example, the public switched telephone network (PSTN), a legacy private branch exchange (PBX), a wireless network (e.g., RAN, code-division multiple access (CDMA) network, time division multiple access (TDMA) network, global system for mobile communications (GSM) network), and/or other circuit-based networks.

Information transfer over transmission medium can be based on one or more communication protocols. Communication protocols can include, for example, Ethernet protocol, Internet Protocol (IP), Voice over IP (VoIP), a Peer-to-Peer (P2P) protocol, Hypertext Transfer Protocol (HTTP), Session Initiation Protocol (SIP), H.323, Media Gateway Control Protocol (MGCP), Signaling System #7 (SS7), a Global System for Mobile Communications (GSM) protocol, a Push-to-Talk (PTT) protocol, a PTT over Cellular (POC) protocol, and/or other communication protocols.

Devices of the computing system can include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a World Wide Web browser (e.g., Microsoft® Internet Explorer® available from Microsoft Corporation, Mozilla® Firefox available from Mozilla Corporation). Mobile computing device include, for example, a Blackberry®. IP phones include, for example, a Cisco® Unified IP Phone 7985G available from Cisco Systems, Inc, and/or a Cisco® Unified Wireless Phone 7920 available from Cisco Systems, Inc.

While the invention has been particularly shown and described with reference to specific illustrative embodiments, it should be understood that various changes in form and detail may be made without departing from the spirit and scope of the invention.

What is claimed:

1. A system for determining a product collapse or eutectic melt temperature during a primary drying phase of freeze drying, the system comprising:
   a freeze dryer including a holder for a product;
   a temperature sensor coupled to the product;
   a three-dimensional imager including a source of radiation and a detector positioned proximate to the holder; and
   a processor coupled to the detector of the three-dimensional imager, the processor configured to receive images from the three dimensional imager, receive information about product temperature from the temperature sensor during freeze drying, and determine the product critical temperature by determining a temperature at which a viscous flow in the product structure occurs during ice sublimation from the received images and the received information about product temperature.

2. The system of claim 1 wherein the three-dimensional imager comprises an optical coherence tomography (OCT) system.

3. The system of claim 1 wherein the temperature sensor comprises one or more thermocouples configured to contact the product.

4. The system of claim 1 wherein the temperature sensor comprises one or more resistance temperature detectors configured to monitor product temperature.

5. The system of claim 1 wherein the temperature sensor comprises an infrared detector configured to monitor product temperature.

6. The system of claim 1 wherein the holder is configured to hold one or more vials capable of containing the product.

7. The system of claim 1 wherein the product is contained within a container.

8. The system of claim 7 wherein the processor is further configured for determining the temperature at which the viscous flow in the product structure occurs during ice sublimation while the product is contained within the container.

9. A system for measuring an onset of viscous flow and consolidation of pores in a dry layer of a sample during freeze drying, the system comprising:
   a freeze dryer including a holder for the sample;
   a three-dimensional imager including a source of radiation and a detector positioned proximate to the holder; and
   a processor coupled to the detector of the three-dimensional imager, the processor configured to receive images from the three dimensional imager and determine a pore structure characteristic within the sample from the images.

10. The system of claim 9 wherein the sample is contained within a container.

11. The system of claim 10 wherein the processor is further configured to determine the pore structure characteristic within the sample from the images while the sample is contained within the container.

* * * * *